United States Patent
Kurz et al.

[11] Patent Number: 5,979,235
[45] Date of Patent: Nov. 9, 1999

[54] TEST BODY FOR TESTING ITEMS OF CLOTHING

[76] Inventors: Bernhard Kurz, Oeffelstr. 5, 81543 Munich; Wolfgang Uedelhoven, Zugspitzstr. 39, 85435 Erding, both of Germany

[21] Appl. No.: 08/999,709

[22] Filed: Oct. 8, 1997

[30] Foreign Application Priority Data

Oct. 15, 1996 [EP] European Pat. Off. ............ 96116522

[51] Int. Cl.$^6$ ............................................. G01F 15/14
[52] U.S. Cl. ......................................................... 73/432.1
[58] Field of Search .................... 73/432.1, 159, 73/172, 865.6, 866; 374/141, 142

[56] References Cited

U.S. PATENT DOCUMENTS

| | | | |
|---|---|---|---|
| 3,595,070 | 7/1971 | Smith | 73/159 X |
| 4,432,223 | 2/1984 | Paquette et al. | 73/73 X |
| 4,536,971 | 8/1985 | Pulsmeier et al. | 73/159 X |
| 4,799,384 | 1/1989 | Casall . | |
| 4,918,981 | 4/1990 | Gore | 73/38 X |
| 4,961,339 | 10/1990 | Kleis et al. | 73/73 |
| 5,121,630 | 6/1992 | Calvin | 73/73 |
| 5,226,318 | 7/1993 | Huber et al. | 73/159 |
| 5,329,807 | 7/1994 | Sugar et al. | 73/38 X |
| 5,361,450 | 11/1994 | Shofner et al. . | |
| 5,500,635 | 3/1996 | Mott | 374/141 X |
| 5,535,617 | 7/1996 | Bastianelli | 73/40 |
| 5,537,868 | 7/1996 | Shofner et al. | 73/160 |
| 5,610,344 | 3/1997 | Ueda et al. | 73/865.6 |
| 5,631,429 | 5/1997 | Cutright et al. | 73/865.5 |

FOREIGN PATENT DOCUMENTS

| | | |
|---|---|---|
| 0 604 874 A2 | 12/1993 | European Pat. Off. . |
| 604874 | 7/1994 | European Pat. Off. . |
| 0 368 716 | 10/1989 | France . |
| 0 353 524 | 7/1989 | Germany . |
| XP000196876 | 10/1995 | Germany . |
| 58-021164 | 4/1983 | Japan . |
| 58-88659 | 5/1983 | Japan . |
| 60 06863 | 1/1995 | Japan . |
| 8-047484 | 6/1996 | Japan . |
| 2 272 528 | 5/1994 | United Kingdom . |
| WO 9320437 | 10/1983 | WIPO . |

*Primary Examiner*—Richard Chilcot
*Assistant Examiner*—Jewel V. Thompson
*Attorney, Agent, or Firm*—Gary A. Samuels

[57] ABSTRACT

A test body (10) for testing apparel items is described. The body has air entry means (20) for supplying conditioned gas into the inner of the test body, air exit means (30) for allowing the exit of said conditioned gas from the inner of the test body, and at least one perforation (60) through a side wall (50) of the test body (10) for allowing the conditioned air within the test body (10) to come into contact with an inner side of the apparel item. The pressure difference of said conditioned gas measured between the inner side of the apparel item and the air exit means is (30) less than 10%, preferably less than 5%, and more preferably substantially zero, when said conditioned gas has 0% humidity.

12 Claims, 3 Drawing Sheets

TEST BODY FOR TESTING ITEMS OF CLOTHING

FIELD OF THE INVENTION

The invention is directed to a test body for testing apparel items.

BACKGROUND OF THE INVENTION

Test systems for testing apparel items are known, for example, from WO-A-90/04772 (W. L. Gore & Associates, Inc.), or from WO-A-93/20437 (BASTIANELLI) (W. L. Gore & Associates (UK) Ltd.). These methods involve filling the apparel item, in both instances footwear, with water. In the '772 publication, the moisture vapour transmission rate through the fabric of which the shoe is made, is measured. In the '437 publication, a shoe construction is tested for leaks.

JP-A-58-21164 (HARADA) assigned to Toyo Boseki K.K. discloses a test apparatus for simulation of the effects of weather on clothes. This application discloses a wind tunnel to produce wind which is passed over a humidity bath. The apparel item is placed over a box containing a fluid which is intended to model the skin of the wearer of the apparel item.

JP-A-60-6863 (AMAMIYA) assigned to Unitaka K.K. teaches a pair of temperature and humidity control chambers. In the connecting outlet between the two chambers an item of apparel is placed and the effect of the climate on the apparel is determined by changing the conditions within each of the chambers separately from one another.

JP-A-58-88659 (HARADA) assigned to Toyo Boseki K.K. teaches an artificial skin plate consisting of a metal plate on a fluid container. The metallic plate has number of pores to model the sweat production of a human being.

An article in the German language magazine Schuh-Technik, 10/95, pp 16–20 entitled "Faktoren des Schutragekomforts—Bedeutung und Quantifizierung" by Prof. Dr. Bernhard—KURZ describes the importance of determining accurate measurements of the effect of climate on the wearer of apparel items. The described test system consists of a climate chamber in which the humidity and temperature can be varied in accordance with the conditions that are to be tested.

In order to make accurate measurements of the comfort of various apparel items, it is also necessary to be able to model the effects of sweating of the wearer of the item. Until now, the available test bodies have not accurately modelled the effect of sweating. The bodies have either relied on forcing conditioned air through the fabric or by using a heated, damp surface.

At this point it should be noted that the term "conditioned air" is to be understood as referring to a gas—in particular a gas mixture such as that found in air—in which water vapour has been added in controlled amounts and the gas has been heated to desired values. Such a system is known from JP-A-21164 (HARADA) or from EP-A-0 604 874 (SHOFNER et al) assigned to Zellweger Uster, Inc. By conditioning the air, various climates can be simulated ranging from tropical climates to arctic climates. The gas mixture could, depending on the conditions to be modelled, be varied from the general composition of air to special compositions or by the use of other gases.

SUMMARY OF THE INVENTION

It is therefore an object of the invention to provide an improved test body for use in a apparel testing system.

It is furthermore an object of the invention to provide an improved test body which accurately models the sweating of the human body.

These and other objects of the invention are achieved by ensuring that the pressure difference of said conditioned gas measured between the inner side of the apparel item and the air exit means of the test body is less than 10%, preferably less than 5%, and more preferably substantially zero, when said conditioned gas has 0% humidity.

When this condition is achieved, little or none of the conditioned gas is forced through the fabric of which the apparel item is made. Since the wearer of the apparel item has no in-built "ventilator" which under real life conditions forces conditioned air or sweat through the fabric, this ensures that sweating conditions can be accurately modelled and tested. The pressure difference must be measured at substantially 0% humidity since the fabric is generally designed to allow water vapour to pass though it either through a wicking process or by capillary action. This will lead to a drop in the pressure difference when the conditioned air in the inner of the test body is humid.

In order to accurately simulate the human body, the test body has a plurality of perforations in the side walls whose size and distribution are designed to simulate sweat glands of a human body by arranging the perforations according to the sweat gland density of the human body.

The best test results are obtained when the conditioned air within the test body is substantially uniform in humidity and temperature. This is achieved by providing an air exit means with at least one extension tube extending into the interior of the test body. Additionally the test body further comprises a ventilator situated within the test body for mixing and distributing evenly the conditioned gas within the inside of the test body. Furthermore a distribution tube is attached to an air-entry means for distributing the conditioned air evenly around the interior of the test body.

Measurements of the humidity and temperature within the test body are carried out with first temperature and/or humidity sensors in the inner of the test body. A second set of temperature and/or humidity sensors are provided on the outside of the side wall of the test body for measuring the temperature and/or humidity of the conditioned gas outside the test body. These sensors are connected to data collection apparatus for collecting and analysing the results obtained from the measurements.

DETAILED DESCRIPTION OF THE INVENTION

Figure 1:
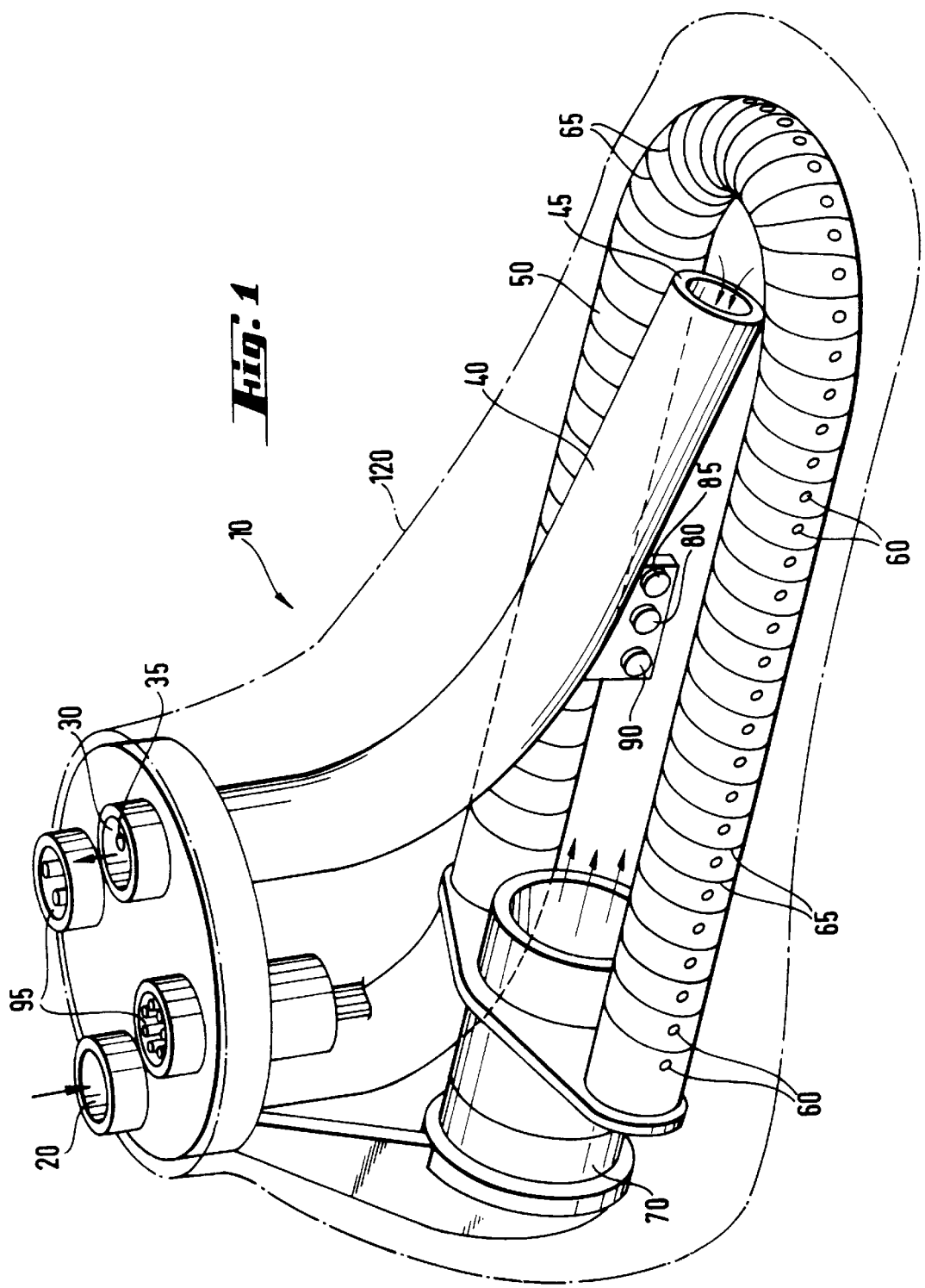
FIG. 1 shows a view of the interior of a test body.

FIG. 1 shows a test body (10) according to the invention. In the figure the test body (10) is depicted as being in the shape of a foot. However, the test body allows a variety of structures to be constructed and the depicted body is not intended to be limiting. For example, the test body could be in the shape of a hand or of a torso. The test body need also not take a particular shape. For some purposes, it is convenient to use a box-like shape onto which uncut fabric is placed for testing its properties under climatic conditions.

Referring again to FIG. 1, the test body (10) is provided with air entry means (20) for feeding a supply of conditioned air into the inner of the test body and air exit means (30) for allowing the conditioned air to exit from the inner of the test body (10). In a preferred embodiment of the invention, an extension tube (40) is connected to the air exit means (30) for allowing the conditioned air to be collected from a particular point within the test body (10). Use of the extension tube (40) has the advantage that a more even distribution of the conditioned air can be achieved within the test body (10). If, for example, no extension tube (40) were to be provided, then at the extremities of the test body (10), the circulation of the conditioned air might not be sufficient to simulate the desired conditions. In a test body (10) modelled on the shape of a foot such as that depicted in FIG. 1, then the distal end (45) of the extension tube (40) is preferably situated in the toe region. In a test body (10) modelled on the shape of a hand, then it would be advantageous to have a plurality of extension tubes (40) whose distal ends (45) would be situated at the extremities of the fingers.

The air entry means (20) is connected to a distribution tube (50) for distributing the conditioned air within the test body (10). The distribution tube (50) has at least one hole (60) for allowing the conditioned air to pass from the distribution tube (50) into the inner of the test body (10). Preferably the distribution tube (50) has a plurality of holes (60) for allowing an even distribution of the conditioned air within the inner of the test body (10). The size and spacing of the holes (60) can be altered to achieve a defined pressure drop along the length of the tube and thus to ensure the optimal distribution of conditioned air within the test body (10). The distribution tube (50) is preferably supplied with heating elements (65) for warming the distribution tube and thus ensuring that condensation does not occur on the inner and/or outer surface of the distribution tube (50).

Furthermore with additional heating elements (65) within the test body (10), a quick change of climate is achievable. The combination of the heating elements (65) with the conditioned air can ensure that optimised temperature and humidity stabilisation are achieved.

The test body (10) can furthermore be provided with a ventilator (70) for producing air currents within the inner of the test body (10) and thus further ensuring an even distribution of air within the test body (10).

Within the test body (10), a first humidity sensor (80) and a first temperature sensor (90) are provided. These elements are shown illustratively in FIG. 1 as being positioned in the middle of the test body (10). They can, of course, be positioned anywhere within the inner of the test body (10) depending on wherever one wishes to obtain measurements. The first humidity sensor (80) and first temperature sensor (90) are connected by means of an electrical connection (95) to the outside of the test body (10) and thus to the data collection apparatus (not shown).

Figure 2:
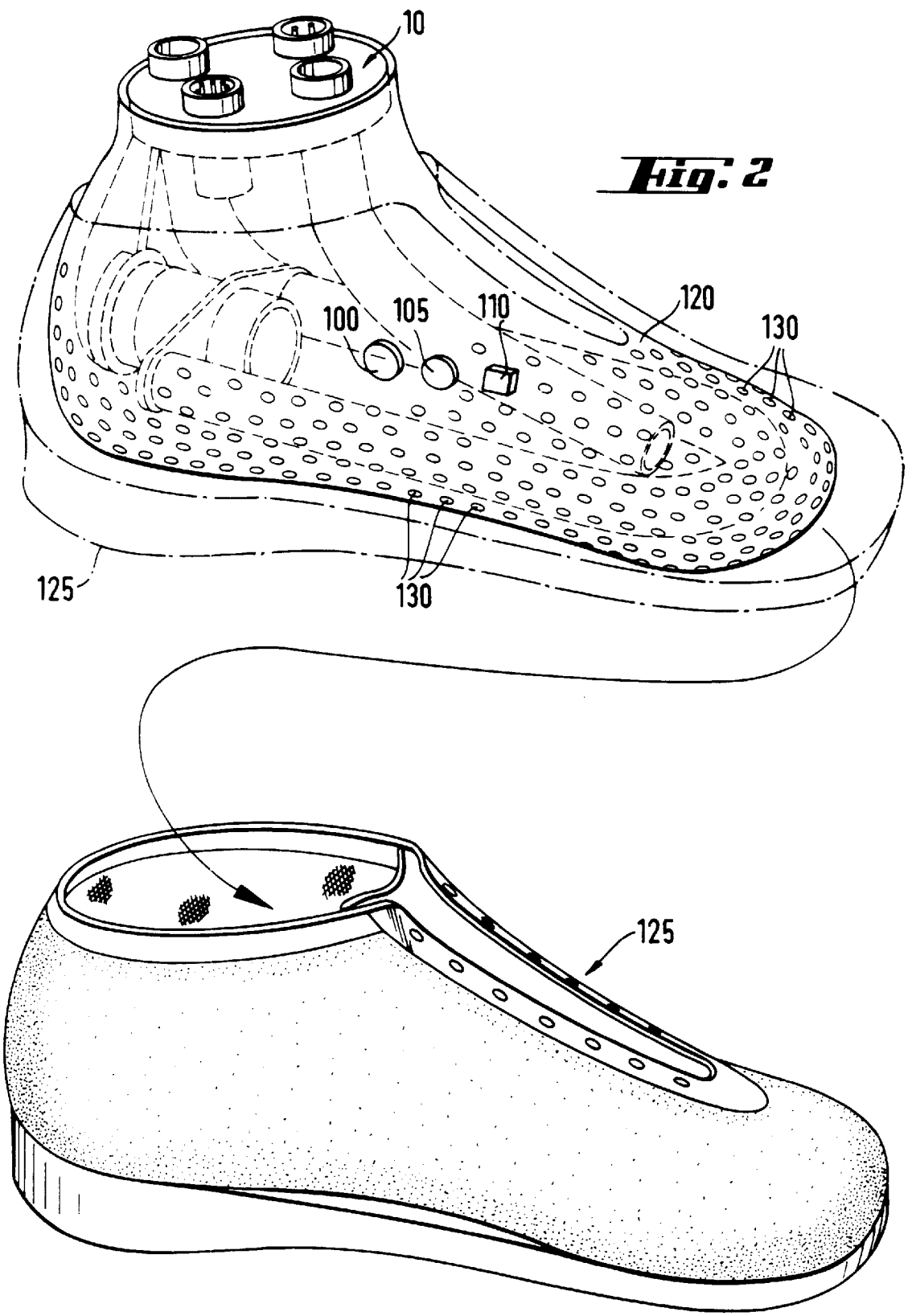
FIG. 2 shows the outer covering of a test body.

The test body (10) is surrounded by a covering (120) as is shown in FIG. 2 which is formed in the shape of the part of the human body on which the test body (10) is modelled. This covering can be an air-tight fabric or membrane material. The item of apparel which is to be tested is placed on this covering (120). For example, an apparel item such as a shoe (125) is slipped over the covering depicted in FIG. 2. The covering (120) has at least one perforation (130) and preferably many more. The size, shape and distribution of the perforations (130) can be altered to meet the test conditions required. In the preferred embodiment of the invention, the perforations are modelled on the shape and distribution of the human sweat glands. The distribution of sweat glands within the human body has been described in the art. For example, in a foot it is know that there are a large number of seat glands in the instep whereas in the heel area and around the toes there are few sweat glands. The perforations (130) in the covering (120) are consequently provided so that more conditioned air passes through the covering (120) in the area of the foot instep whereas very little or none passes through the covering (120) in the heel area or around the toes. By using this distribution, tests can be carried out on the items of apparel in which human sweating conditions can be accurately modelled.

On the outside of the covering (120), a second temperature sensor (100) and a second humidity sensor (105) are mounted. These are depicted in an illustrative and non-limiting manner in FIG. 2. These second sensors (100, 105) are used to measure the temperature and humidity conditions on the outside of the covering (120) and thus on the inside of the apparel item (125). The second temperature sensor (100) and the second humidity sensor (105) are connected to the data collection apparatus by electrical connections (not shown). Pressure sensor 3J measures the air pressure at the air exit and pressure sensor 85 measures the pressure at the inner side of the apparel item. A pressure sensor (110) can also be mounted on the surface of the covering to measure the pressure of the conditioned air on the outside of the perforation (130).

In operation, the test apparatus is supplied with conditioned air through the air entry means (20) and distribution tube (50). The air circulates in the inner of the test body (10) and is evenly distributed by the ventilator (70). The ventilator is a standard ventilator which is commercially available. It is provided with a plurality of blades for circulating the conditioned air within the inner of the test body (70). The ventilator is either driven very slowly or is pulse driven so that the air is smoothly distributed within the inner of the test body (70). The conditioned air is conditioned to contain a certain percentage of humidity by humidifying means. These humidifying means are known in the prior art. As an example, European Patent Application EP-A-604 874 or Japanese Patent Application JP-A-58-21164 can be referenced. The degree of humidity and the temperature at which the air is supplied are chosen to simulate human sweating conditions during particular activities. These values are chosen by reference to measurements made on test human subjects.

Through the perforations (130) in the covering (120), the conditioned air comes into contact with the tested item of apparel (125). Some of the water vapour contained within the conditioned air passes through item of apparel and thus simulates sweating by a human being. However, preferably, little or none of the gases (such as oxygen or nitrogen) within the conditioned air pass through the item of apparel. Little or none of the gases other than water vapour pass through the item of apparel because there is no pressure difference driving the gases through the fabric. When the air outside of the test body (10) has substantially zero humidity and the air within the test body (10) is conditioned then there is a partial water vapour pressure difference between the inside of the test body, i.e., one side of the item of apparel, and the outside of the test body, i.e., on the other side of the item of apparel. Thus there is transport of water through the fabric of the item of apparel. These gases are collected by the distribution tube (40) and pass out of the test body (10) by means of the air exit means (30). Measurements of the humidity of the air exited from the test body (10) allow a calculation to be made of the total amount of moisture which passes through the item of apparel (125). Individual measurements can be made by means of the first and second temperature and humidity sensors (80, 90, 100, 105). These measurements can be collected by data collection means and evaluated. More temperature and humidity sensors can be used if required.

As ideally, none of the gases within the conditioned air pass through the fabric of the item of apparel (125), this means that conditioned air with zero humidity, i.e. totally dry air, should be passed through into the shoe, there should be no pressure difference between the air entry means (20), the air exit means (30) and the outside of the perforation (130) or, indeed, between any two of these points. In practice, however, a small difference is noted as will be illustrated by means of the following examples:

When humid conditioned air is passed into the test body, the pressure difference between the same points becomes a function of the amount of water vapour that is passed through the fabric of the item of apparel (125). For example, when testing clothing or footwear made from a liquid water impermeable, water vapour permeable material, such as GORE-TEX® fabric, the pressure difference becomes a function of the so-called MVTR (moisture vapour transmission rate—see PCT patent application WO-A-90/04772 (GORE)—or a discussion of this subject) as well as the shape and distribution of the perforations (130).

Figure 3:
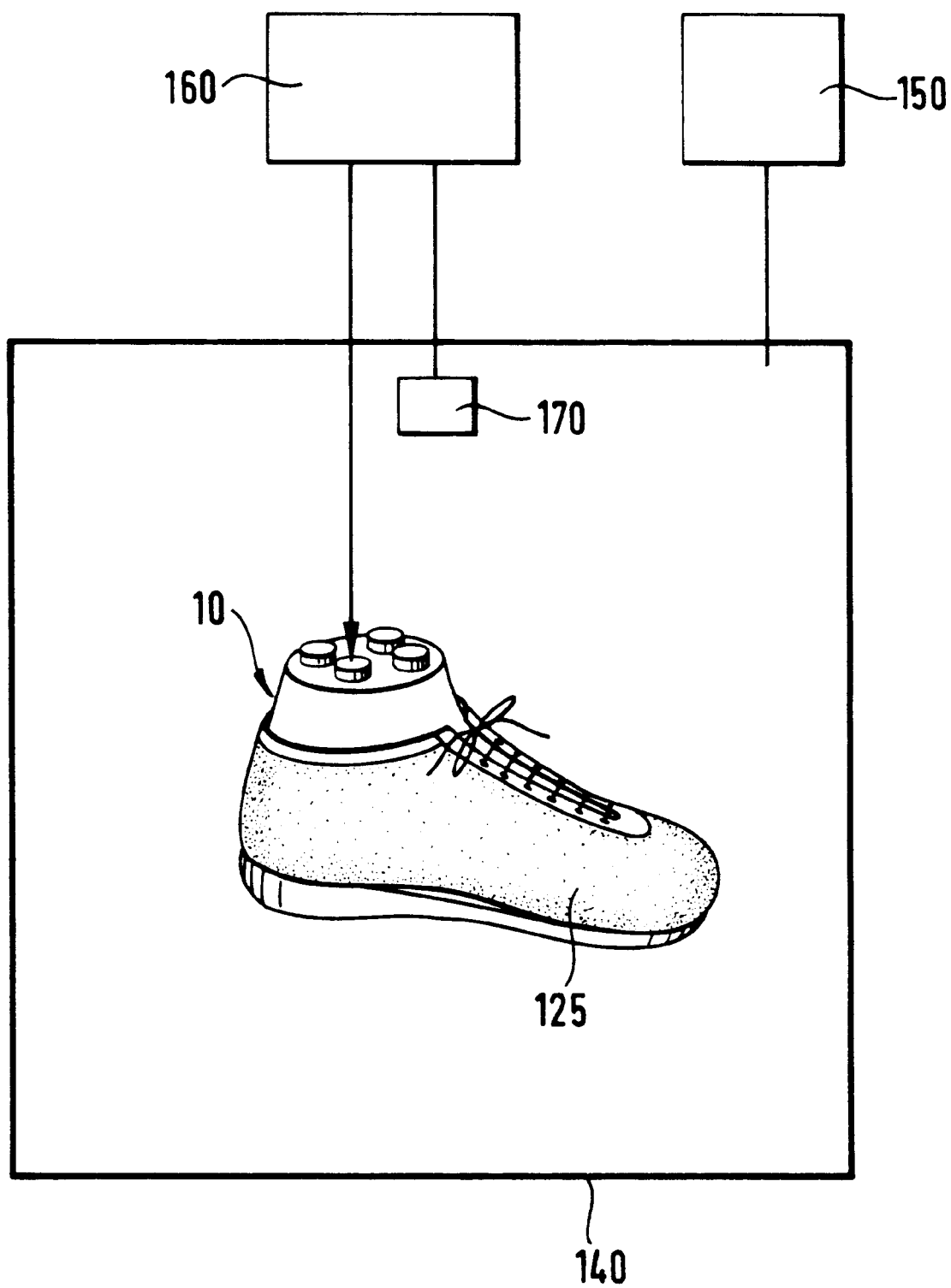
FIG. 3 shows a climate chamber.

The test body (10) is used in a climate control chamber (140) as shown in FIG. 3 which has control means (150) for controlling the temperature and humidity of the climate, data collection means (160) connected to the first and second humidity and temperature sensors (80, 90, 100, 105) as well as third sensors (170) for measuring the humidity and temperature of the climate chamber (140) itself. The data collection means (160) analyses the results obtained and is able to evaluate the results by reference to stored data based on the results obtained from tests made on human beings. Although a few exemplary embodiments of the present invention have been described in detail above, those skilled in the art readily appreciate that many modifications are possible without materially departing from the novel teachings and advantages which are described herein. Accordingly, all such modifications are intended to be included within the scope of the present invention, as defined by the following claims.

We claim:

1. Test body having an inner and an outer side for testing apparel items having an inner side and an outer side, the test body comprising an air entry for supplying conditioned gas into the inner of the test body, an air exit for allowing the exit of said conditioned gas from the inner of the test body, at least one perforation through a side wall of the test body for allowing said conditioned gas within the test body to come into contact with an inner side of the apparel item; and wherein pressure difference of said conditioned gas supplied into the inner of the test body during operation of said test body measured between the inner side of the apparel item and the air exit is less than 10% when said conditioned gas has 0% humidity and the humidity of the air on the outer side of said test body is 0%.

2. Test body according to claim 1 wherein the test body has a plurality of perforations in the side walls.

3. Test body according to claim 2 wherein the plurality of perforations are of a size and distribution to simulate sweat glands of a human body.

4. Test body according to claim 1 wherein the air entry means further comprises a distribution tube within the test body for evenly distributing the condition gas throughout the interior of the test body.

5. Test body according to claim 4 wherein the distribution tube is provided with at least one heating element for warming the distribution tube.

6. Test body according to claim 1 wherein the air exit means further comprises at least one extension tube in the inner of the test body.

7. Test body according claim 1 wherein the test body further comprises a ventilator situated in the inner of the test body for distributing the conditioned gas within the inner of the test body.

8. Test body according to claim 1 further comprising:

first temperature sensors in the test body for measuring the temperature of the conditioned gas within the test body.

9. Test body according to claim 1 further comprising:

first humidity sensors in the test body for measuring the humidity of the conditioned gas within the test body.

10. Test body according to claim 8 further comprising:

second temperature sensors on the outside of the side wall of the test body for measuring the temperature of the conditioned gas outside the test body.

11. Test body according to claim 9 further comprising second humidity sensors on the outside of the side wall of the test body for measuring the humidity of the conditioned gas outside the test body.

12. Process for testing apparel items which comprises:

a) providing a test body defined in claim 1;

b) providing an item of apparel around the test body;

c) supplying conditioned air through the air entry and distribution tube;

d) collecting the conditioned gas as it passes out of the test body through the air exit;

e) measuring the humidity of the exited air;

wherein the pressure difference of the conditioned gas measured between the inner side of the apparel item and the air exit means is less than 10%.

* * * * *